United States Patent [19]

Laurent

[11] Patent Number: 5,795,915
[45] Date of Patent: Aug. 18, 1998

[54] USE OF (X-AMINOMETHYL-3,4-DICHLOROBENZYL) THIOACETAMIDE DERIVATIVES FOR INHIBITING DOPAMINE REUTAKE AND NEW COMPOUNDS FOR THIS USE

[75] Inventor: Philippe Laurent, Oullins, France

[73] Assignee: Laboratoire L. Lafon, Maisons Alfort, France

[21] Appl. No.: 649,530

[22] Filed: May 17, 1996

[30] Foreign Application Priority Data

May 19, 1995 [FR] France .................. 95 06000

[51] Int. Cl.$^6$ ............................. A61K 31/555
[52] U.S. Cl. ................ 514/567; 514/618; 514/645
[58] Field of Search .................. 514/567, 618, 514/645

[56] References Cited

FOREIGN PATENT DOCUMENTS 0 158 545  10/1985  European Pat. Off. .
0 406 088   1/1991  European Pat. Off. .

OTHER PUBLICATIONS

Chemical Abstracts AN 1990:491276, Allan et al Jan.
Chemical Abstracts AN 1995:802729, Smolders et al Jan.

*Primary Examiner*—Keith MacMillan
*Attorney, Agent, or Firm*—Jacobson, Price, Holman & Stern, PLLC

[57] ABSTRACT

The invention relates to the use of a compound selected from:

[α-(tert-butylaminomethyl)-3,4-dichlorobenzyl] thioacetamide and its laevorotatory isomer,

[α-(tert-amylaminomethyl)-3,4-dichlorobenzyl] thioacetamide and its isomers,

[α-(1-adamantylaminomethyl)3,4-dichlorobenzyl] thioacetamide and its isomers, as well as the addition salts of these compounds with pharmaceutically acceptable acids, for inhibiting dopamine reuptake.

18 Claims, No Drawings

USE OF (X-AMINOMETHYL-3,4-DICHLOROBENZYL) THIOACETAMIDE DERIVATIVES FOR INHIBITING DOPAMINE REUTAKE AND NEW COMPOUNDS FOR THIS USE

The present invention relates to the use in therapy of some (α-aminomethyl-3,4-dichlorobenzyl)thioacetamide derivatives.

The present invention relates more specifically to the use of these compounds for inhibiting dopamine reuptake.

In EP-0,158,545, a description has already been given of a class of compounds of formula

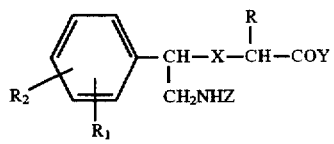

in which X is S or SO,

Y is a $C_1$–$C_4$alkoxy group or an $NH_2$ or NHOH group,

Z is a $C_1$–$C_4$alkyl group,

R is H or $CH_3$, and $R_1$ and $R_2$ represent H, F, Cl or Br.

These compounds have been described as antidepressants.

In EP-0,406,088, a description has, in addition, been given of [α-(tert-butylaminomethyl)-3,4-dichlorobenzyl] thioacetamide and its addition salts with pharmaceutically acceptable acids. This compound has also been described as an antidepressant and for promoting food intake.

The present invention is based on the discovery that:

[α-(tert-butylaminomethyl)-3,4-dichlorobenzyl] thioacetamide and its laevorotatory isomer,

[α-((tert-amylaminomethyl)-3,4-dichlorobenzyl] thioacetamide and its isomers,

[α-(1-adamantylaminomethyl)-3,4-dichlorobenzyl] thioacetamide and its isomers, as well as the addition salts of these compounds with pharmaceutically acceptable acids, are potent inhibitors of dopamine reuptake, and may accordingly be used in therapy.

Consequently, the present invention relates to the use of a compound selected from:

[α-(tert-butylaminomethyl)-3,4-dichlorobenzyl] thioacetamide and its laevorotatory isomer,

[α-(tert-amylaminomethyl)-3,4-dichlorobenzyl] thioacetamide and its isomers,

[α-(1-adamantylaminomethyl)-3,4-dichlorobenzyl] thioacetamide and its isomers, as well as the addition salts of these compounds with pharmaceutically acceptable acids, for the manufacture of a medicinal product which inhibits dopamine reuptake.

The outcome of inhibiting dopamine reuptake is an increase in the concentration of dopamine and of 3-methoxytyramine (3MT) in the synaptic space without modifying the concentrations of 3,4-dihydroxyphenylacetic acid (DOPAC) and of homovanillic acid (HVA). This property manifests itself in an increase in the functioning of the central dopaminergic pathways, which is appraised objectively by behavioural modifications such as the appearance of stereotyped movements, an increase in locomotor activity and a reduction in the period of immobility in animals subjected to the test of "behavioural despair".

As a result of their properties of inhibition of dopamine reuptake, the compounds may be used in the following indications:

anhedonia, that is to say loss of interest and a withdrawal from all the usual pleasurable activities, stimulation of cognition, catatonic-type schizophrenia (according to DSM IV Classification), Parkinson's disease, pharmacological dependence on drugs such as cocaine.

For the first four indications, there exists a deficiency of functioning of the central dopaminergic systems, which may be corrected by inhibiting dopamine reuptake, the outcome of which is an improvement in dopaminergic transmissions resulting from the economical use of the dopamine synthesized and released.

For the last indication, pharmacological dependence on drugs such as cocaine, substances which inhibit dopamine reuptake bind to the site of transport of dopamine and hence compete for this site with drugs such as cocaine, thereby preventing these drugs from acting.

In these indications, the compounds may be administered orally at daily doses of 0.01 to 10 mg/kg, and preferably 0.1 to 5 mg/kg.

More generally, the compounds may be administered to man or animals orally or parenterally.

The compounds are generally administered in the form of solid, semi-solid or liquid compositions.

As examples of compositions, tablets, hard gelatin capsules, suppositories, solutions or suspensions for injection may be mentioned, as well as retard forms and slow-release implanted forms. In these compositions, the active principle is generally mixed with one or more customary pharmaceutically acceptable excipients well known to a person skilled in the art.

Among the compounds defined above, preference is given to [α-(tert-butylaminomethyl)-3,4-dichlorobenzyl]-thioacetamide and most especially the laevorotatory isomer, that is to say (−)-[α-(tert-butylaminomethyl)-3,4-dichlorobenzyl]thioacetamide and its addition salts with pharmaceutically acceptable acids.

The present invention also relates to this isomer and its addition salts with pharmaceutically acceptable acids.

The present invention relates, in addition, to

[α-(tert-amylaminomethyl)-3,4-dichlorobenzyl] thioacetamide, and its isomers and the addition salts of these compounds with pharmaceutically acceptable acids,

[α(1-adamantylaminomethyl)-3,4-dichlorobenzyl] thioacetamide, its isomers and the addition salts of these compounds with pharmaceutically acceptable acids.

The isomers of [α-(tert-butylaminomethyl)-3,4-dichlorobenzyl]thioacetamide may be obtained by separating the diastereoisomeric salts formed, respectively, with 1(−)-malic acid and d(+)-malic acid and racemic methyl [α-(tert-butylaminomethyl)-3,4-dichlorobenzyl]-thioacetate, and ammonolysis of each of the isomers separated.

The compounds containing a tert-amyl or 1-adamantyl group may be obtained according to processes similar to those described in EP-A-0,158,545 and EP-A-0,406,088.

The examples which follow illustrate the preparation of the new compounds.

EXAMPLE 1

Preparation of 1(−)-[α-(tert-butylaminomethyl)-3,4-dichlorobenzyl]thioacetamide hydrochloride (CRL 41 789)

(1) Preparation of methyl (−)-[α-(tert-butyl-aminomethyl)-3,4-dichlorobenzyl]thioacetate 1(−)-malate A solution of 42.4 g (0.121 mol) of racemic methyl [α-(tert-butylaminomethyl)-3,4-dichlorobenzyl]-thioacetate (see EP-A-0.406.088) in 100 ml of ethyl acetate is mixed at 20° C. with a solution of 8.2 g (0.061 mol) of l(−)-malic acid in 200 ml of ethyl acetate, the mixture is cooled and the product is drained and recrystallized three times in 250 ml of ethyl acetate each time, until a precipitate having a melting point of 113°–114° C. is obtained.

The l(−)-malate of the l(−)-amino ester is obtained in a 35% yield.

(2) Preparation of 1(−)-|α-(tert-butylaminomethyl)-3,4-dichlorobenzyl|thioacetamide hydrochloride (CRL 41 789).

18 g (0.043 mol) of the above l(−)-malate, dissolved in 200 ml of methanol, are treated with 100 ml of 28% aqueous ammonia; the mixture is stirred for 5 hours, the reactants are left in contact overnight, the methanol is evaporated off under vacuum, the residue is taken up with water and extracted with $CH_2Cl_2$, the organic phase is washed with water, dried and evaporated, the oily residue is taken up with 50 ml of acetone and acidified with 10 ml of a 5N solution of hydrochloric acid in isopropanol, the product is drained and dried and the compound is obtained in a 24% yield.

The product is a cream-coloured powder; it is soluble in water and ethanol; and insoluble in ether and ethyl acetate.

It melts at 170° C. and has a specific rotation α=−95°±5° (2% $CH_3OH$).

EXAMPLE 2

Preparation of d(+)-|α-(tert-butylaminomethyl)-3,4-dichlorobenzyl]thioacetamide hydrochloride (CRL 41 790)

(1) Preparation of methyl d(+)-[α-(tert-butyl-aminomethyl)-3,4-dichlorobenzyl]thioacetate d(+)-malate A solution of 29 g (0.083 mol) of methyl [α-(tert-butylaminomethyl)-3,4-dichlorobenzyl]thioacetate (racemic mixture recovered after separation of CRL 41 789, consisting preponderantly of the dextro-rotatory isomer) in 50 ml of ethyl acetate is mixed at 20° C. with a solution of 5.6 g (0.042 mol) of d(+)-malic acid in 250 ml of ethyl acetate, the mixture is cooled and the product is drained and recrystallized twice in 200 ml of ethyl acetate, until a precipitate having a melting point of 114° C. is obtained.

The d(+)-malate of the d(+)-amino ester is obtained in a 50% yield.

(2) Preparation of d(+)-[α-(tert-butylamino-methyl)-3,4-dichlorobenzyl]thioacetamide hydrochloride (CRL 41 790)

18 g (0.043 mol) of the above d(+)-malate, dissolved in 200 ml of methanol, are treated with 100 ml of 28% aqueous ammonia; the mixture is stirred for two hours and the reactants are left in contact for 24 hours at room temperature.

The methanol is evaporated off under vacuum, the residue is taken up with water and extracted with $CH_2Cl_2$, the organic phase is washed with water, dried and evaporated, the residue is taken up with 50 ml of acetone and acidified with 10 ml of a 5N solution of hydrochloric acid in isopropanol and the product is drained.

The compound is obtained in a 22% overall yield. It takes the form of a pinkish powder. It is soluble in water, ethanol and methanol, and insoluble in ether and ethyl acetate; it melts at 170° C. and has a specific rotation α=+91°±5° (2% $CH_3OH$).

EXAMPLE 3

Preparation of |α-(tert-amylaminomethyl)-3,4-dichlorobenzyl|thioacetamide hydrochloride (CRL 42 059)

(1) Preparation of 1-(3,4-dichlorophenyl)-2-(tert-amylamino)ethanol hydrochloride 27 g (0.1 mol) of 1-(3,4-dichlorophenyl)-2-bromoethanol are added in the cold state to a solution of 37.5 g (50 ml) (0.43 mol) of 2-methyl-2-butylamine, 100 ml of ethanol and 0.5 g of KI. After 48 hours in contact at 20° C. and 3 hours under reflux, the mixture is filtered, the filtrate is evaporated under vacuum, the residue is taken up with ether and the organic phase is washed with water. 200 ml of N HCl are added, and the product is drained and washed with 20 ml of cold water and with ether. The hydrochloride (m.p.= 184°–185° C.) is obtained in a 78% yield.

(2) Preparation of 1-(3,4-dichlorophenyl)-2-(tert-amylamino)-1-chloroethane hydrochloride A solution of 15 ml of $SOCl_2$ in 40 ml of $CH_2Cl_2$ is added to a suspension of 23.4 g (0.075 mol) of the above alcohol hydrochloride in 75 ml of $CH_2Cl_2$. The mixture is heated to reflux for 5 hours and left standing overnight, and the product is drained and washed with twice 20 ml of $CH_2Cl_2$. The hydrochloride (m.p.=200°–202° C.) is obtained in a 72% yield.

(3) Preparation of methyl [α-(tert-amylamino-methyl)-3,4-dichlorobenzyl]thioacetate A solution of sodium methylate is prepared by dissolving in the cold state 2.3 g (0.1 g-at.) of sodium in 120 ml of methanol.

5 ml (0.05 mol) of methyl thioglycolate and 16.55 g (0.05 mol) of the above hydrochloride are added in the cold state with stirring. The mixture is stirred for one hour at room temperature and 5 hours under reflux. After the mixture has stood overnight, the NaCl is filtered off, the methanol is evaporated off under vacuum, the residue is taken up with ether, the organic phase is washed with water and extracted with N HCl, precipitation is induced in the cold state with 3N NaOH, extraction is performed with ether, and the organic phase is washed with water, dried and evaporated.

The oily ester is obtained in a 90% yield.

(4) Preparation of [α-(tert-amylaminomethyl)-3,4-dichlorobenzyl]thioacetamide hydrochloride (CRL 42 059)

16 g (0.044 mol) of the above amino ester, dissolved in 120 ml of methanol, are treated with 40 ml of 28% $NH_4OH$. After 48 hours in contact at 20° C., the methanol is driven off under vacuum, the residue is taken up with water and extracted with ether, the latter is extracted with N HCl, precipitation is induced with concentrated NaOH, extraction is performed with ether, the organic phase is washed with water, dried and evaporated and the base (m.p.=84° C.) is crystallized in isopropyl ether.

This base, dissolved in 100 ml of ethyl acetate, is acidified with a solution of HCl in isopropanol. The product is drained and recrystallized in ethanol/ethyl acetate and the compound is obtained in a 60% yield.

The product is a white powder; it is soluble in water and alcohols; and insoluble in ether and ethyl acetate. It melts at 155°–156° C.

EXAMPLE 4

Preparation of |α-(1-adamantylaminomethyl)-3,4-dichlorobenzyl|thioacetamide hemifumarate (CRL 42 060)

(1) Preparation of 1-(3,4-dichlorophenyl)-2-(1-adamantylamino)ethanol hydrochloride 27 g (0.1 mol) of 1-(3,4-dichlorophenyl)-2-bromoethanol are added to a solution of 30 g (0.2 mol) of 1-adamantamine, 0.1 g of KI and 100 ml of ethanol; the mixture is stirred for 48 hours at 20° C. and 6 hours under reflux.

The methanol is evaporated off under vacuum, and the residue is taken up with 200 ml of ether and 30 ml of 3N HCl; the product is drained and washed with twice 20 ml of cold water and with ether. The hydrochloride (m.p.= 258°–260° C.) is obtained in a 70% yield.

(2) Preparation of 1-(3,4-dichlorophenyl)-2-(1-adamantylamino)-1-chloroethane hydrochloride 15 ml of $SOCl_2$ in 40 ml of $CH_2Cl_2$ are added to a suspension of 25 g (0.066 mol) of the above amino alcohol hydrochloride in 60 ml of $CH_2Cl_2$.

After 4 hours under reflux and standing over-night, the product is drained and washed with $CH_2Cl_2$ and with ether. The chloro compound is obtained in a 94% yield. It sublimes without melting from 250° C.

(3) Preparation of methyl |α-(1-adamantylaminomethyl)-3,4-dichlorobenzyl|thioacetate hydrochloride A solution of sodium methylate is prepared with 2.76 g (0.12 g-at.) of sodium and 150 ml of methanol. 6 ml (0.06 mol) of methyl thioglycolate and 23.7 g (0.06 mol) of the above chloro compound are added in the cold state. The mixture is stirred for one hour at room temperature and 5 hours under reflux.

After one night in contact, the NaCl is filtered off, the methanol is evaporated off under vacuum, the residue is taken up with water and extracted with ether and the organic phase is washed with water. 30 ml of 3N HCl are added, the mixture is stirred and the product is drained and washed with twice 20 ml of cold $H_2O$ and with ether.

The precipitate is suspended in 500 ml of $H_2O$, neutralized with $Na_2CO_3$ and extracted with $CH_2Cl_2$. The organic phase is washed, dried and evaporated, the residue is taken up with ethyl acetate and the organic phase is acidified with a 5N solution of hydrogen chloride in isopropanol. The product is drained and washed with ethyl acetate, and the amino ester hydrochloride (m.p.=153°–154° C.) is obtained in a 65% yield.

(4) Preparation of [α-(1-adamantylaminomethyl)-3,4-dichlorobenzyl]thioacetamide hemifumarate A cold solution of 15.5 g (0.033 mol) of the above amino ester hydrochloride in 150 ml of methanol is saturated with ammonia. 10 ml of $NH_4OH$ are added, and a further 10 ml of $NH_4OH$ 24 hours later.

The reactants are left in contact for 48 hours, monitoring the formation of the amide by TLC. The methanol is evaporated off under vacuum, the residue is taken up with water and extracted with ether, and the organic phase is washed with water, dried and evaporated.

The oily residue is taken up with 30 ml of ethanol, 2 g of fumaric acid are added and the product is drained and washed with 5 ml of cold ethanol and 20 ml of AcOEt. It is recrystallized in ethanol, and the compound is obtained in a 77% yield.

It takes the form of a white powder.

It is soluble in methanol and DMSO, and insoluble in water, ether and ethyl acetate. It melts at 188° C.

Results of pharmacological tests will be given below, demonstrating, in particular, the effects at the site of dopamine reuptake by the compounds used in the invention, giving, by way of comparison, the results obtained with the dextrorotatory isomer of |α-(tert-butylaminomethyl)-3,4-dichlorobenzyl|thioacetamide.

Inhibition of binding at the site of dopamine reuptake in vitro in rat striatum Rats, (male, CD Sprague-Dawley, 200–250 g) are sacrificed by decapitation. The striata are removed immediately and then stored at −80° C. until used. On the day of the manipulation, the striata are thawed, coated with buffer and then brought into suspension. This suspension is then poured into the centrifuge tubes, made up to 10 ml with pH 7.7 buffer (50 mM Tris (HCl), 120 mM NaCl, 5 mM KCl) and thereafter centrifuged at 20,000 rpm for 15 minutes. The pellet is resuspended in 10 ml of buffer and is then subjected to a second centrifugation (20,000 rpm for 15 minutes). The above procedure is repeated, so that the homogenate undergoes a third centrifugation identical to the previous two. The pellet thereby obtained is suspended in a few ml of buffer and then homogenized. The membrane suspension is then diluted in a requisite volume. Increasing concentrations of the test compounds dissolved in the buffer are distributed. Aliquots of the membrane suspension are then added. The radioactive ligand ([$^3$H]mazindol), used as a label of the type of site studied, is then distributed manually in the tubes, which are thereafter incubated (final volume 1 ml).

The reaction is stopped by filtration through a Harvester system (Whatman GF/B filter strip). The filter strip is then washed three times with 5 ml of buffer before being placed in an automatic cutting system.

The cut filters fall into counting vials, and 4 ml of scintillation fluid are distributed automatically by the system. Each sample is subjected to counting of the radioactivity using a liquid scintillation counter.

Three series of tests (test 1, test 2 and test 3) are carried out with each compound for determination of the $IC_{50}$, each determination being carried out on two different samples.

The specific binding is defined as the difference between the total binding and the non-specific binding (displaced by an excess of non-radioactive ligand). The values obtained in counts per minute (cpm) are then converted into disintegrations per minute (dpm) in accordance with the efficiency of the counter.

The $IC_{50}$ is defined as the concentration of the substance under study needed to displace 50% of the specifically bound radioactive label.

The experimental data emanating from the liquid scintillation counter (Kontron) are stored on diskette, managed by a program (Convert) and then analysed by means of Ligand* software, which calculates the 50% inhibitory concentration ($IC_{50}$) and the inhibition constant Ki $$Ki = \frac{IC_{50}}{1 + [L]/Kd}$$

where [L] represents the concentration of the radioactive ligand and Kd the dissociation constant of this same ligand.

(The values of the $IC_{50}$ and of Ki are inversely proportional to the affinity of the product under study for the binding site.

The mean $IC_{50}$ and Ki values obtained are given in Table I.

The $LD_0$ and $LD_{100}$ values in mice via the i.p. route are also given in this table.

TABLE I

| Compound | Code | Toxicity mg/kg | | Inhibition of binding at the site of dopamine reuptake | |
|---|---|---|---|---|---|
| | | $LD_0$ | $LD_{100}$ | $IC_{50}$ | Ki |
| R = tert-butyl, racemate, hydrochloride | CRL 41 414 | 128 | 256 | $3.1 \times 10^{-8}$ | $6.3 \times 10^{-8}$ |
| R = tert-butyl, laevorotatory isomer, hydrochloride | CRL 41 789 | 64 | 256 | $4.4 \times 10^{-8}$ | $2.4 \times 10^{-8}$ |
| R = tert-butyl, dextrorotatory isomer, hydrochloride | CRL 41 790 | 128 | 512 | $1.1 \times 10^{-6}$ | $6.2 \times 10^{-7}$ |
| R = tert-amyl, racemate, hydrochloride | CRL 42 059 | 30 | 256 | $7.4 \times 10^{-8}$ | $4.6 \times 10^{-8}$ |
| R = 1-adamantyl, racemate, hydrochloride | CRL 42 060 | 128 | 1024 | $4.0 \times 10^{-8}$ | $4.4 \times 10^{-8}$ |

Effect on the extracellular levels of neuro-mediators and metabolites in anaesthetized rat striatum (intracerebral microdialysis)

This determination is obtained by high performance liquid chromatography coupled with an electro-chemical detection.

HPLC: Spherisorb cartridge, ODS-2 (5 µm), L=125M, ∅=4 mm, Merck. Mobile phase: 0.1M potassium phosphate, 0.1M citric acid, octane-sulphonic acid 50 mg/l, 0.1 mM EDTA, 4% methanol, pH 4.80, pump output 0.9 ml/min electrochemical detection: BAS detector, LC-4C, +750 mV analyser: Millenium, Waters Rats (male, Sprague-Dawley, CD, Charles River, 280–300 g) anaesthetized with chloral hydrate (400 mg/kg, i.p.) are placed in a stereotactic apparatus. The microdialysis probe (CMA/11 L=3 mm, ∅=0.24 mm, Carnegie) is implanted according to the coordinates of the Paxinos and Watson atlas in the anterior portion of the left striatum: I=10, L=2.4, H=−6.1.

Ringer's fluid ($CaCl_2$=2.4 mM, KCl=4 mM, NaCl=147 mM) is perfused at 2 µl/min into the probe. The dialysates collected every 20 minutes are cooled (to approximately 6° C.) and then analysed.

After one hour of collection, groups of 6 rats receive intraperitoneally in a volume of 5 ml/kg:

either an injection of isotonic sodium chloride solution, or the test compound dissolved in distilled water at doses of 16, 32 or 64 mg/kg.

In the dialysate, the dopamine (DA), 3,4-dihydroxyphenylacetic acid (DOPAC), homovanillic acid (HVA) and 3-methoxytyramine (3MT) concentrations are measured by electrochemical detection and quantified with respect to a standard series, and are corrected in accordance with the efficiency of the probe determined in vitro before each test.

Only tests in which the probes display an efficiency of more than 5% are taken into account.

With the compound CRL 41 789, a significant increase is observed in the dopamine and 3MT concentrations without modification of the DOPAC and HVA concentrations, which confirms the results obtained in the dopamine inhibition test. It should be noted that, in contrast, the dextrorotatory isomer (CRL 41 790) does not cause any modification of the dopamine and 3MT concentrations.

Induction of stereotyped movements in rats

Groups of 6 rats (male, CD, Sprague-Dawley, Charles River, 160–200 g) receive CRL 41 789 or CRL 41 790 intraperitoneally in distilled water (5 ml/kg), and are immediately placed in Plexiglas cages (20×10×10 cm). The stereotyped movements are scored from 0 to 3 every 10 minutes until they have disappeared.

With the compound CRL 41 789 at doses of 16 and 32 mg/kg, the appearance of intense and lasting stereo-typed movements is observed. In contrast, it should be noted that the compound CRL 41 790 does not cause the appearance of any stereotyped movement, even at the high dose of 128 mg/kg.

Effects on the locomotor activity of mice

Half an hour after receiving CRL 41 789 or CRL 41 790 intraperitoneally in distilled water, groups of 6 to 24 mice (male, NMRI, C.R.E. Janvier, 18–22 g) are placed individually in crossed-beam activity cages, where their locomotor activity (number of rays crossed) is recorded over 30 minutes.

With the compound CRL 41 789 at doses of 2, 8 and 32 mg/kg, a marked and statistically significant increase in the locomotor activity of the mice is observed, the increase rising with the dose. In contrast, it should be noted that the compound CRL 41 790 does not give rise to any increase in the locomotor activity of the mice, even at the high dose of 64 mg/kg.

Effects on the test of "behavioural despair" in mice

Half an hour after receiving CRL 41 789 or CRL 41 790 intraperitoneally in distilled water, groups of 6 or 12 mice (male, CD1, Charles River, 18–22 g) are placed individually in a high vessel made of transparent glass, filled with water to a height of 6 cm. The total period of immobility between the beginning of the 3rd minute and the end of the 6th minute following immersion of the animal is noted.

With the compound CRL 41 789 at doses of 0.5, 2, 8 and 32 mg/kg, a decrease in the period of immobility is observed, the decrease rising with the dose. This effect is marked and statistically significant at the doses of 8 and 32 mg/kg. In contrast, it should be noted that the compound CRL 41 790 does not give rise to any decrease in the period of immobility of the mice, even at the high dose of 64 mg/kg.

I claim:

1. A method for the treatment of anhedonia, which comprises administering to a patient in need thereof an effective amount of a compound selected from the group consisting of:

[α-(tert-butylaminomethyl)-3,4-dichlorobenzyl] thioacetamide and its levorotatory isomer;

[α-(tert-amylaminomethyl)-3,4-dichlorobenzyl] thioacetamide and its isomers; and

[α-(1-adamantylaminomethyl)-3,4-dichlorobenzyl] thioacetamide and its isomers; as well as addition salts of the compound with pharmaceutically acceptable acids.

2. A method for stimulating cognition, which comprises administering to a patient in need thereof an effective amount of a compound selected from the group consisting of:
- [α-(tert-butylaminomethyl)-3,4-dichlorobenzyl] thioacetamide and its levorotatory isomer;
- [α-(tert-amylaminomethyl)-3,4-dichlorobenzyl] thioacetamide and its isomers; and
- [α-(1-adamantylaminomethyl)-3,4-dichlorobenzyl] thioacetamide and its isomers; as well as addition salts of the compound with pharmaceutically acceptable acids.

3. A method for the treatment of catatonic type schizophrenia, which comprises administering to a patient in need thereof an effective amount of a compound selected from the group consisting of:
- [α-(tert-butylaminomethyl)-3,4-dichlorobenzyl] thioacetamide and its levorotatory isomer;
- [α-(tert-amylaminomethyl)-3,4-dichlorobenzyl] thioacetamide and its isomers; and
- [α-(1-adamantylaminomethyl)-3,4-dichlorobenzyl] thioacetamide and its isomers; as well as addition salts of the compound with pharmaceutically acceptable acids.

4. A method for the treatment of Parkinson's disease, which comprises administering to a patient in need thereof an effective amount of a compound selected from the group consisting of:
- [α-(tert-butylaminomethyl)-3,4-dichlorobenzyl] thioacetamide and its levorotatory isomer;
- [α-(tert-amylaminomethyl)-3,4-dichlorobenzyl] thioacetamide and its isomers; and
- [α-(1-adamantylaminomethyl)-3,4-dichlorobenzyl] thioacetamide and its isomers; as well as addition salts of the compound with pharmaceutically acceptable acids.

5. A method for the treatment of drug dependency, which comprises administering to a patient in need thereof an effective amount of a compound selected from the group consisting of:
- [α-(tert-butylaminomethyl)-3,4-dichlorobenzyl] thioacetamide and its levorotatory isomer;
- [α-(tert-amylaminomethyl)-3,4-dichlorobenzyl] thioacetamide and its isomers; and
- [α-(1-adamantylaminomethyl)-3,4-dichlorobenzyl] thioacetamide and its isomers; as well as addition salts of the compound with pharmaceutically acceptable acids.

6. A method for the treatment of dependency on drugs that limit dopamine uptake, which comprises administering to a patient in need thereof an effective amount of a compound selected from the group consisting of:
- [α-(tert-butylaminomethyl)-3,4-dichlorobenzyl] thioacetamide and its levorotatory isomer;
- [α-(tert-amylaminomethyl)-3,4-dichlorobenzyl] thioacetamide and its isomers; and
- [α-(1-adamantylaminomethyl)-3,4-dichlorobenzyl] thioacetamide and its isomers; as well as addition salts of the compound with pharmaceutically acceptable acids.

7. The method of claim 1, wherein the compound is [α-(tert-butylaminomethyl)-3,4-dichlorobenzyl] thioacetamide or its levorotatory isomer.

8. The method of claim 7, wherein the compound is the levorotatory isomer.

9. The method of claim 2, wherein the compound is [α-(tert-butylaminomethyl)-3,4-dichlorobenzyl] thioacetamide or its levorotatory isomer.

10. The method of claim 9, wherein the compound is the levorotatory isomer.

11. The method of claim 3, wherein the compound is [α-(tert-butylaminomethyl)-3,4-dichlorobenzyl] thioacetamide or its levorotatory isomer.

12. The method of claim 11, wherein the compound is the levorotatory isomer.

13. The method of claim 4, wherein the compound is [α-(tert-butylaminomethyl)-3,4-dichlorobenzyl] thioacetamide or its levorotatory isomer.

14. The method of claim 13, wherein the compound is the levorotatory isomer.

15. The method of claim 5, wherein the compound is [α-(tert-butylaminomethyl)-3,4-dichlorobenzyl] thioacetamide or its levorotatory isomer.

16. The method of claim 15, wherein the compound is the levorotatory isomer.

17. The method of claim 6, wherein the compound is [α-(tert-butylaminomethyl)-3,4-dichlorobenzyl] thioacetamide or its levorotatory isomer.

18. The method of claim 17, wherein the compound is the levorotatory isomer.

* * * * *